(12) United States Patent
Oleksy

(10) Patent No.: US 9,844,763 B2
(45) Date of Patent: Dec. 19, 2017

(54) METHOD OF PREHEATING DEHYDROGENATION REACTOR FEED

(71) Applicant: Technip Process Technology, Inc., Houston, TX (US)

(72) Inventor: Slawomir A. Oleksy, Billerica, MA (US)

(73) Assignee: Technip Process Technology, Inc., Houston, TX (US)

(*) Notice: Subject to any disclaimer, the term of this patent is extended or adjusted under 35 U.S.C. 154(b) by 0 days.

(21) Appl. No.: 14/674,433

(22) Filed: Mar. 31, 2015

(65) Prior Publication Data

US 2016/0288079 A1    Oct. 6, 2016

(51) Int. Cl.
| | | |
|---|---|---|
| C07C 5/327 | (2006.01) |
| C07C 5/367 | (2006.01) |
| B01J 19/00 | (2006.01) |
| F28D 15/00 | (2006.01) |
| B01J 8/04 | (2006.01) |

(52) U.S. Cl.
CPC ......... *B01J 19/0013* (2013.01); *B01J 8/0403* (2013.01); *B01J 8/0446* (2013.01); *B01J 8/0492* (2013.01); *B01J 8/0496* (2013.01); *C07C 5/327* (2013.01); *F28D 15/00* (2013.01); *B01J 2208/0053* (2013.01); *B01J 2208/00176* (2013.01); *B01J 2208/00256* (2013.01); *B01J 2208/00274* (2013.01); *B01J 2208/00309* (2013.01); *B01J 2208/00371* (2013.01); *B01J 2208/00504* (2013.01); *B01J 2219/00103* (2013.01); *B01J 2219/00121* (2013.01)

(58) Field of Classification Search
CPC ............................... C07C 5/327; C07C 5/367
USPC .................. 585/440, 441, 910, 911
See application file for complete search history.

(56) References Cited

U.S. PATENT DOCUMENTS

| | | | |
|---|---|---|---|
| 3,660,510 | A | 5/1972 | Kindler et al. |
| 4,628,136 | A | 12/1986 | Sardina |
| 4,695,664 | A | 9/1987 | Whittle |
| 4,769,506 | A | 9/1988 | Kosters |
| 5,053,572 | A | 10/1991 | Kim et al. |
| 7,922,980 | B2 | 4/2011 | Oleksy et al. |
| 8,084,660 | B2 | 12/2011 | Welch et al. |

(Continued)

FOREIGN PATENT DOCUMENTS

| | | |
|---|---|---|
| WO | WO 2014/035398 A2 | 3/2014 |
| WO | WO 2010/142944 A1 | 9/2014 |
| WO | WO 2014/142994 A1 | 9/2014 |

OTHER PUBLICATIONS

PCT Notification of Transmittal of the International Search Report and the Written Opinion of the International Searching Authority, or the Declaration dated Jul. 1, 2016 of International Application No. PCT/US16/24642, filed Mar. 29, 2016.

*Primary Examiner* — Thuan D Dang
(74) *Attorney, Agent, or Firm* — Locke Lord LLP; Alan B. Clement; Peter J. Fallon

(57) ABSTRACT

Methods and systems for heating a reactor feed in a multi reactor hydrocarbon dehydrogenation process. The methods and systems are advantageously employed for the production of styrene by the catalytic dehydrogenation of ethylbenzene. The catalytic dehydrogenation process employs heating steam operating at a steam to oil ratio of about 1.0 or less and relatively low steam superheater furnace temperature, such that all components exposed to steam in the process (outside of the fired heaters) can be constructed with standard metallurgy.

25 Claims, 7 Drawing Sheets

(56) References Cited

U.S. PATENT DOCUMENTS

| | | |
|---|---|---|
| 8,163,971 B2 | 4/2012 | Wilcox et al. |
| 8,193,404 B2 | 6/2012 | Welch et al. |
| 2010/0240940 A1 | 9/2010 | Wilcox et al. |
| 2010/0305374 A1 | 12/2010 | Iaccino et al. |

METHOD OF PREHEATING DEHYDROGENATION REACTOR FEED

TECHNICAL FIELD

The various embodiments of the present invention relate to methods and systems having improved energy efficiencies in the production of styrene by dehydrogenation of ethylbenzene. The methods and systems reduce utility cost and provide savings in comparison with the current technology practiced in the industry.

BACKGROUND

It is well known in the art of styrene manufacture to react ethylbenzene (EB) in the presence of steam over a dehydrogenation catalyst, such as iron oxide under dehydrogenation reaction conditions, in order to strip hydrogen from the ethyl group on the benzene ring to form styrene. It is also well known that the dehydrogenation of ethylbenzene requires large amounts of energy, for example, in the form of steam.

Alternative methods for reducing energy consumption (i.e., steam) in processes for producing styrene via dehydrogenation of ethylbenzene have been previously described.

U.S. Pat. No. 4,628,136 to Sardina discloses a dehydrogenation process for producing styrene from ethylbenzene in the presence of steam by recovering heat of condensation normally lost during separation of the various components and using the heat to vaporize an aqueous feed mixture of ethylbenzene and water. Sardina teaches that this obviates the need to use steam to vaporize the liquid ethylbenzene feed.

U.S. Pat. No. 4,695,664 to Whittle discloses a means for recovering waste heat from a low temperature process stream with a vaporizable heat sink liquid and two immiscible liquids that form a low boiling azeotrope. The heat sink liquid is brought into indirect heat exchange with the low temperature process stream, whereby the heat sink liquid is able to recover heat from the process stream.

Various methods have been proposed that allow use of azeotropic heat recovery while operating at the minimum ratio of reaction steam to ethylbenzene, as determined by catalyst stability (i.e., resistance to coking). Such methods include use of direct heating as described in U.S. Pat. Nos. 8,193,404 and 8,084,660 to Welch et al., which discloses among other things methods for increasing the efficiency of a dehydrogenation unit by use of at least one direct heating unit.

Method of providing heat for chemical conversion and a process and system employing the method for the production of olefin to U.S. Pat. No. 8,163,971 to Wilcox et al. addresses the problem of supplying heat to the system at an overall steam/oil weight ratio of 1.0 or lower. Generally, these ratios would require steam temperature at the outlet of the steam superheater to be increased to 950° C., or even higher. At such high temperatures, the use of special and costly metallurgy is required.

U.S. Pat. No. 7,922,980 to Oleksy et al. discloses methods for recovering the heat of condensation from overhead vapor produced during ethylbenzene-to-styrene operations. In this regard, the '980 patent uses the overhead of an EB/SM splitter column to vaporize an azeotropic mixture of ethylbenzene and water.

Other methods that could be employed to enable the use of azeotropic heat recovery while operating at the minimum ratio of reaction steam to ethylbenzene involve passing the reactor feed mixture through the convection section of a fired heater, as practiced by The Dow Chemical Company as described in U.S. Pat. No. 4,769,506 to Kosters.

Use of a split reheater arrangement as disclosed in published International Application No.: PCT/US2012/053100, Pub. No. W0/2014/035398, makes it possible to reduce the heating steam to ethylbenzene ratio required for interstage reheat to as low as 0.34 kg per kg of ethylbenzene. However, heating the primary reactor to a temperature required for efficient conversion of the ethylbenzene remains a separate problem.

Additionally, International Application No.: PCT/US2013/032244, Pub. No. W0/2014/142994, relates to efficiencies in the production of styrene through reduced quantities of steam used in the disclosed process. However, there still remains a need in the art for improvements that can provide even greater efficiencies through lower heating steam to ethylbenzene ratio, as presented herein. Without a means of supplying heat to the primary reactor feed prior to the addition of superheated steam, the temperature of the superheated steam added to the reactor feed upstream of the first reactor would exceed the mechanical temperature limits of the steam transfer line and the mixing device. To bring the temperature down, the amount of reaction steam has to be increased, which increases the overall energy demand of the process.

Thus, for economic reasons and process efficiencies, it is desirable to lower the reaction steam to hydrocarbon ratio of the process due to the costs incurred in generating and superheating steam. The inventive methods and systems disclosed herein provide for a reduction of reaction steam/EB ratio while practicing azeotropic heat recovery without resorting to the use of expensive alloys.

SUMMARY OF THE INVENTION

The various embodiments of the invention are directed to advantageously providing heat to processes to produce styrene monomer via ethylbenzene dehydrogenation, especially when the ratio of feed steam to ethylbenzene prior to the addition of superheated steam is greater than or equal to 0.4 by weight, as is the case when ethylbenzene is vaporized as an azeotropic mixture with water.

Consistent with the various embodiments of the present invention, a method of heating a reactor feed in a multi reactor hydrocarbon dehydrogenation process is disclosed, the method comprises the steps of: (i) heating a first reheating steam stream against flue gas from one or more fired heaters, after the reheating steam stream heats a first reactor product stream in one or more first reactor product stream indirect heating apparatuses, to provide a preheating steam stream; (ii) heating a first reactor feed stream comprising a hydrocarbon and optionally feed steam, with the preheating steam stream in a first reactor feed stream indirect heating apparatus prior to entering a first reactor, to provide a preheated hydrocarbon stream and a cooled preheating steam stream; (iii) heating the cooled preheating steam stream in one of the one or more fired heaters to provide a second reheating steam stream; (iv) directing the second reheating steam stream to one of the one or more first reactor product stream indirect heating apparatuses to provide heat to the first reactor product stream and a cooled reheating steam stream; (v) heating the cooled reheating steam in one of the one or more fired heater to provide a heating steam stream; and (vi) mixing the heating steam stream with the preheated hydrocarbon stream prior to entering the first reactor.

Consistent with the various embodiments of the present invention, a method of heating a reactor feed in a multi reactor hydrocarbon dehydrogenation process is disclosed, the method comprises the steps of (i) heating a first reactor feed stream comprising a hydrocarbon, and optionally feed steam, in an indirect heating apparatus with a preheating steam stream from one of one or more fired heater, to provide a preheated hydrocarbon stream and a cooled preheating steam stream; (ii) heating the cooled preheating steam stream against flue gas from the one or more fired heaters to provide a heating steam stream; and (iii) mixing the heating steam stream with the preheated hydrocarbon stream prior to entering a first reactor.

Consistent with the various embodiments of the present invention, a system for heating a reactor feed in a multi reactor hydrocarbon dehydrogenation process is disclosed, the system comprises a means of heating a steam stream used in a prior heat exchange step against flue gas from one or more fired heaters; and a means of indirectly transferring heat from said steam stream to a first reactor feed stream upstream of a first dehydrogenation reactor.

Consistent with the various embodiments of the present invention, a system for heating a reactor feed in a multi reactor hydrocarbon dehydrogenation process is disclosed, the system comprises a means of indirectly transferring heat from a steam stream to a first reactor feed stream in a heat transfer step upstream of a first dehydrogenation reactor to provide a preheated feed stream; and a means of heating the steam stream after the heat transfer step against flue gas from one or more fired heaters; wherein the steam stream, after reheating is mixed with preheated feed stream prior to entering the first dehydrogenation reactor.

The various improvements disclosed herein are substantial in tetras of their economic impact, i.e., through a reduction of energy consumption in the reaction section of a styrene manufacturing facility. Just as important, these improvements do not require fundamental changes to the process, for example, increased temperatures or pressures.

DETAILED DESCRIPTION OF THE INVENTION

Figure 1:
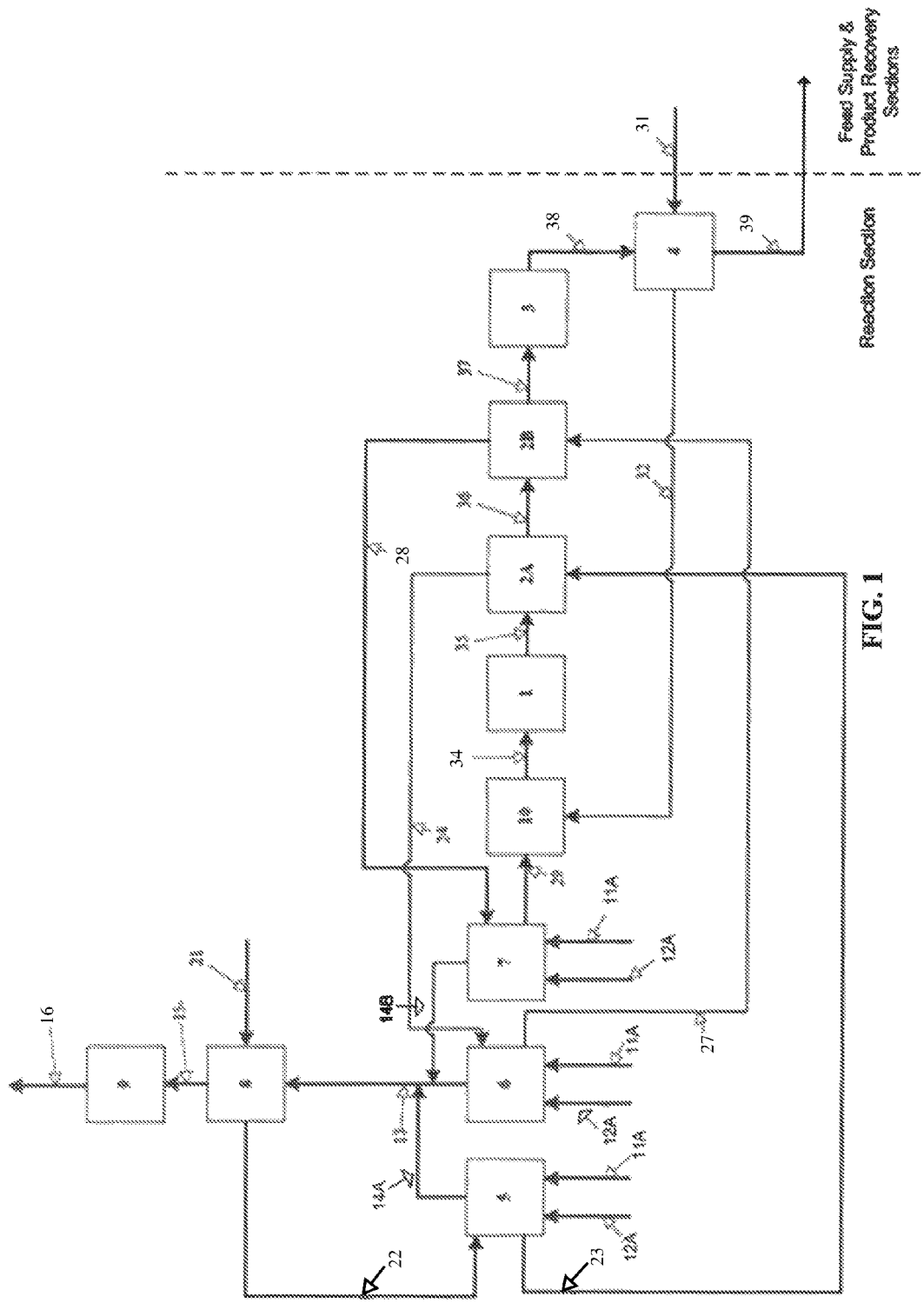
FIG. 1 is a schematic flowsheet illustrating the reaction section of a two-reactor system for the production of styrene via dehydrogenation of ethylbenzene, with steam reheat.

Styrene is one of the most important monomers produced worldwide, and finds major use in the production of polystyrene, acrylonitrile—butadiene—styrene resins (ABS), and a variety of other polymers in the petrochemical industry. Styrene is produced commercially by catalytic dehydrogenation of ethylbenzene, and billions of pounds of styrene are produced each year. Therefore, the investment cost is very high, and even a small improvement in the plant operation can generate significant economic savings. Hence, optimal design and operation of the styrene producing equipment are required in styrene manufacturing processes.

Ethylbenzene dehydrogenation requires large amounts of energy in the form of steam. In particular, the dehydrogenation process requires large amounts of excess "reaction steam," which is the total amount of steam needed to drive the endothermic reaction (i.e., the heat required to moderate the temperature drop as the reaction proceeds), reduce partial pressure of the reactants, and prevent catalyst coking. For the purposes of describing the methods and systems disclosed herein, the steam streams that ultimately constitute the steam that enters the dehydrogenation reactors (collectively referred as "reaction steam") are defined as follows: (1) "feed steam" is steam that enters the process with the hydrocarbon feed, e.g., ethylbenzene feed, at the boundary limit of the system (i.e., the area demarcated by the dotted line in the Figures); (2) "preheating steam" is steam that is used to heat the hydrocarbon feed and feed steam mixture in an indirect heating apparatus, such as a shell-and-tube heat exchanger; (3) "reheating steam" is steam that is used to heat the effluent of a dehydrogenation reactor (before it enters another dehydrogenation reactor immediately downstream of it) in an indirect heating apparatus, and (4) "heating steam" is steam that is directly added to the ethylbenzene feed and feed stream mixture upstream of the first dehydrogenation reactor. As such, the reaction steam is used as a heat transfer medium to heat the reactor feeds in either heat exchangers and/or fired heaters, and feed steam which accompanies the ethylbenzene (EB) feed prevents coking in high temperature heat transfer equipment.

In the conventional ethylbenzene dehydrogenation process for producing styrene, a minimum of about 0.8 kg of heating steam per kg of ethylbenzene feedstock is required for two purposes: (1) reheating the feed steam and ethylbenzene feed between the primary and secondary reactors, which is needed because the dehydrogenation of ethylbenzene is a highly endothermic reaction; and (2) bringing the primary reactor feed steam and ethylbenzene feed mixture to the required reactor inlet temperature.

The ability to reduce the consumption of heating steam is particularly desirable for heat recovery schemes wherein an azeotropic mixture of ethylbenzene and water is boiled against the overhead of the EB/SM Splitter, or against the reactor effluent. The azeotropic mixture contains about 0.5 kg of feed steam per kg of ethylbenzene. An additional 0.10-0.15 kg of feed steam per kg of ethylbenzene can be generated by heat recovery from the reactor effluent, bringing the total feed steam to ethylbenzene ratio to 0.60-0.65 kg/kg. Since the minimum amount of reaction steam (sum of feed steam, preheating steam, reheating steam, and heating steam) is about 1 kg per kg of ethylbenzene, the amount of available heating steam is reduced by more than a factor of 2, i.e., from about 0.80 to about 0.35-0.40 kg per kg of ethylbenzene).

Even though prior art processes make it possible to reduce the heating steam to ethylbenzene ratio to the aforementioned low level for inter-stage reheating (for example, by utilizing the above-referenced split reheater arrangement), heating the feed steam and ethylbenzene feed to the primary dehydrogenation reactor to a temperature required for efficient conversion of the ethylbenzene remains a problem, the overcoming of which is the subject of the instant disclosure. Referring to FIG. 1, the prior art processes are limited because the feed steam and ethylbenzene feed stream 32 leave the feed/effluent exchanger 4 at a temperature that is significantly colder than the required reactor inlet temperature for primary dehydrogenation reactor 1, typically by about 100° C. Thus, the minimum amount of heating steam stream 29 that is necessary to heat the feed steam and ethylbenzene feed to achieve the required temperature for the primary reactor feed stream 34 mixture is fixed by the mechanical limitations of the materials of construction of the steam transfer line for the heating steam stream 29 and primary reactor feed mixer 10. In order to reduce the amount of heating steam for the styrene production process, additional means of heating the ethylbenzene feed is required.

Without a means of adding heat between where the feed steam and ethylbenzene feed leaves the feed/effluent exchanger 4 and the inlet of the primary dehydrogenation reactor 1, heating steam temperatures in excess of 1000° C. are required when the heating steam to ethylbenzene ratio is reduced to less than 0.4 kg per kg of ethylbenzene while keeping the overall reaction steam to hydrocarbon ratio (ethylbenzene) no higher than 1.0. This is well beyond the limits of 800H/800HT metallurgy (899° C. as stated by ASME Code). In order to keep the steam temperature at a level where Alloy 800H/HT can be used, the heating steam flow must be roughly doubled, resulting in an overall reaction Steam-to-Oil ratio (S/O) in the reactors of about 1.25 kg per kg of ethylbenzene (EB) when azeotropic heat recovery is practiced. Since modern ethylbenzene dehydrogenation catalysts are capable of operating at S/O as low as 1.0, it is desirable to reduce the amount of heating steam.

The inventive flow schemes disclosed herein enable practice of azeotropic heat recovery in combination with low heating steam requirements, without the need for expensive and unproven materials of construction.

Figure 2:
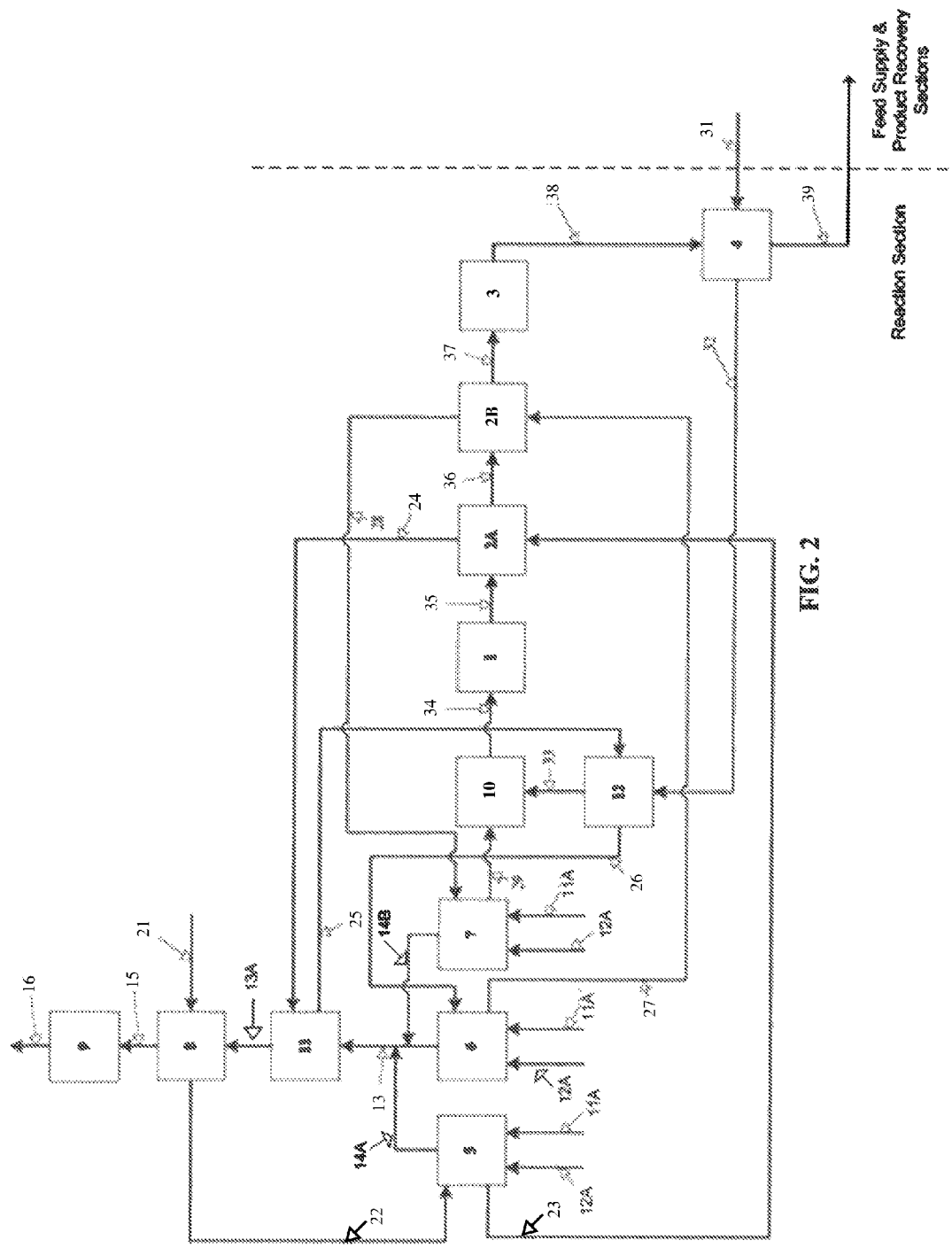
FIG. 2 is a schematic flowsheet illustrating an embodiment of the invention having a two-reactor system and a series of two reheaters for producing styrene via dehydrogenation of ethylbenzene, with steam reheat.
Figure 3:
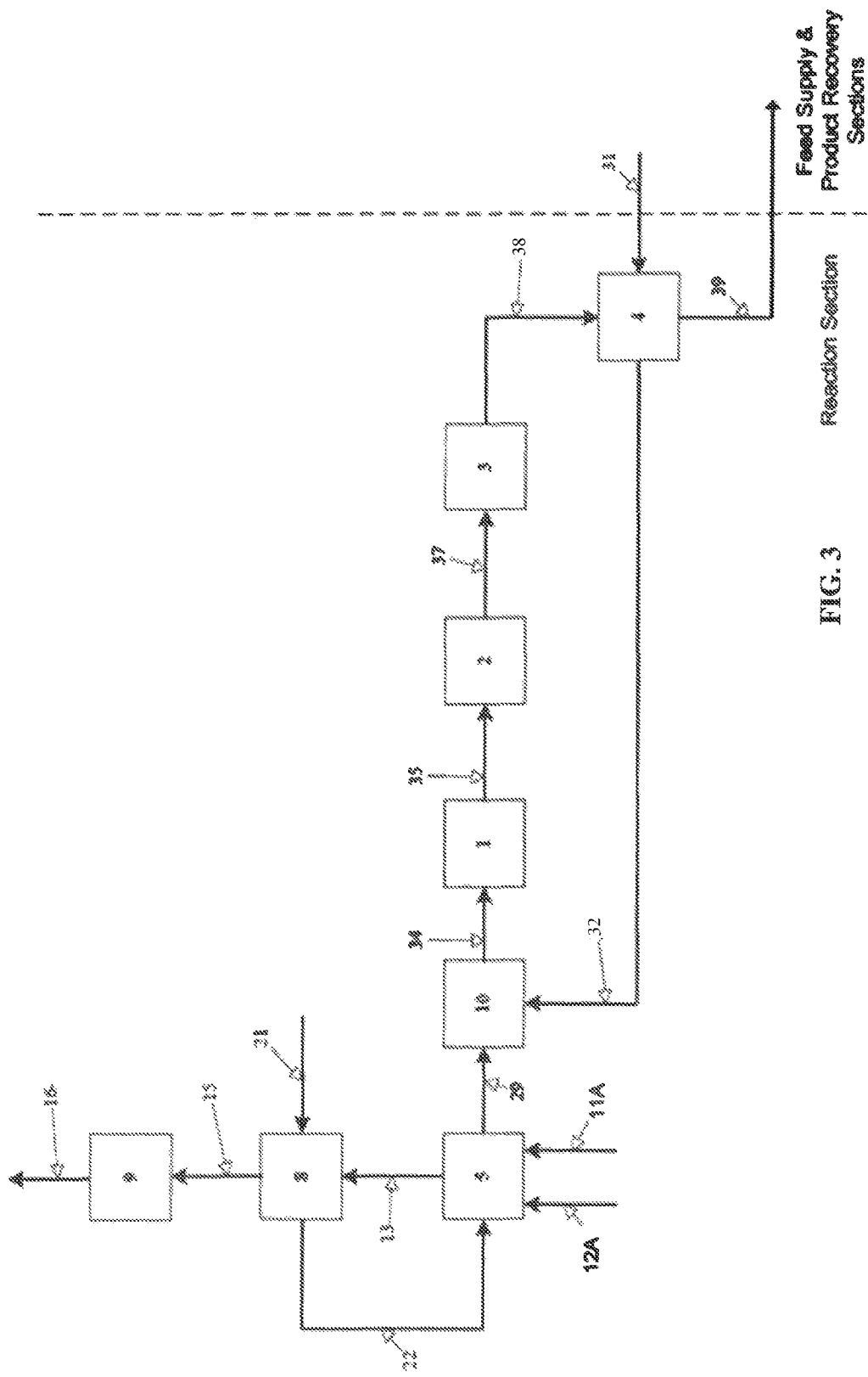
FIG. 3 is a schematic flowsheet illustrating the reaction section of a two-reactor system for the production of styrene via dehydrogenation of ethylbenzene, with direct reheat.

The Figures illustrate the differences between the current state of the art, i.e., FIG. 1 and FIG. 3, and the improved methods of this invention, i.e., FIG. 2 and FIGS. 4-7. Further, it is understood that certain equipment such as valves, piping, indicators and controls, and the like have been omitted from the Figures to facilitate the description thereof, and that the appropriate placement of such equipment is deemed to be within the scope of one skilled in the art.

Referring again to FIG. 1, the mixture of hydrocarbon and feed steam stream 31, (hydrocarbon comprising e.g., ethylbenzene) which is either fully or partially vaporized, enters the shell side of the feed/effluent exchanger 4 where it is heated against the reactor effluent stream 38 from the secondary dehydrogenation reactor 3. The feed steam and reactor feed stream 32 is then directed to the primary reactor feed mixer 10 where it is mixed with the heating steam stream 29 coming from the tertiary steam superheater 7 (steam superheaters as known in the art). The temperature of the superheated steam is adjusted to achieve the desired/required temperature for total primary reactor feed stream 34 mixture, which is transferred to the primary dehydrogenation reactor 1.

Due to the endothermic nature of the dehydrogenation reaction, multiple reactors are required to effect the significant ethylbenzene conversion needed to make the process economic. The inter-stage reheating is typically accomplished in a shell and tube heat exchanger utilizing steam as a heating medium. This type of reheater (i.e., an indirect heating apparatus) is commonly referred to as steam reheater. The reheating can also be accomplished using so called direct heating methods, which include the use of Flameless Distributed Combustion (described in U.S. Pat. No. 8,084,660), or selective oxidation of hydrogen (UOP-Lummus SMART process).

FIGS. 1 and 2 represent a high temperature chemical conversion processes, which utilize two catalytic reactors as conversion apparatuses, i.e., primary (first) dehydrogenation reactor 1 and secondary (second) dehydrogenation reactor 3, respectively, using steam reheat, wherein the reheat duty is split between a series of two reheaters, i.e., primary reheater 2A and secondary reheater 2B, respectively, to provide product stream 39. The reactor effluent stream 35 from primary dehydrogenation reactor 1 is first heated in a series primary reheater 2A against reheating steam stream 23 coming from the primary steam superheater 5 (a fired heater), to produce the reactor effluent stream 36 which is then heated further on the tube side of series secondary reheater 2B against reheating steam stream 27 coming from the secondary steam superheater 6. The temperature of the steam delivered to the primary and secondary reheaters 2A and 2B is adjusted to achieve the desired temperature of process feed stream 37 to the secondary dehydrogenation reactor 3.

The feed stream 31 of FIGS. 1 through 4 provides a process stream for the conversion of a hydrocarbon component in a high temperature chemical conversion process. The process stream, for example, comprises steam and a hydrocarbon component, such as, ethylbenzene that is converted to styrene in the high temperature chemical conversion process.

Further in FIGS. 1 and 2, low temperature steam stream 21 (which ultimately becomes heating steam in all its various applications) is first preheated against the combined flue gas stream 13, i.e., flue gas, (and 13A in FIG. 2)) from the primary, secondary, and tertiary steam superheaters 5, 6 and 7 in primary convective heating coil 8, located in the convection section shared by the superheaters 5, 6 and 7. The steam then passes as stream 22 through the radiant coil of the primary steam superheater 5, and from there it is delivered as reheating steam stream 23 to the primary reheater 2A.

In FIG. 1, the cooled primary reheating steam stream 24 (i.e., after it leaves primary reheater 2A) is heated in the radiant coil of the secondary steam superheater 6 before being sent as secondary reheating steam stream 27 to the secondary reheater 2B. Finally, after leaving reheater 2B the secondary reheating steam stream 28 passes through the radiant coil of the tertiary steam superheater 7 before being added as heating steam stream 29 to the first reactor feed stream 32 in primary reactor feed mixer 10 to bring the resulting final mixture of primary reactor feed stream 34 to the required temperature before entering primary reactor 1.

In FIGS. 1 and 2, heat to the superheaters 5, 6 and 7 is supplied by combustion of fuel 11A in air 12A, which provides for combined flue gas 13 (and combined flue gas 13A in FIG. 2). The flue gas 15 leaving primary convective heating coil 8 is directed to an economizing coil 9 prior to being vented to atmosphere through stack 16.

Some of the difference between the prior art process of FIG. 1, as described above and the processes of the various embodiments of the instant invention, as presented in FIG. 2, comprises the addition of a secondary convection heating coil 11 and a reactor feed preheater 12 apparatus (i.e., an indirect heating apparatus). Cooled reheating steam stream 24 exiting the primary reheater 2A is heated against the combined superheater flue gas streams 13 in secondary convection heating coil 11 and then directed to the shell side of the process feed preheater 12 as preheating steam stream 25 where it exchanges heat with the reactor feed stream 32. Cooled preheating steam stream 26 leaves process feed preheater 12 and is directed to the radiant coil of the secondary steam superheater 6 before being sent as secondary reheating steam stream 27 to secondary reheater 2B.

In FIG. 2, since the temperature of the preheated feed stream 33 (i.e., heated hydrocarbon stream) entering the primary reactor feed mixer 10 is higher than that of corresponding reactor feed stream 32 in the prior art process of FIG. 1, the temperature of the superheated heating steam stream 29 necessary to achieve the same temperature in the primary reactor feed stream 34 (i.e., a mixed reactor feed stream) mixture at the inlet to the primary dehydrogenation reactor 1 is reduced compared with the process of prior art FIG. 1. Alternatively, keeping the tertiary steam superheater 7 outlet temperature the same as in the current state of the art process, the amount of heating steam required is reduced. This reduction in heating steam is illustrated by Example 1 in Table 1.

i.e., the prior art process. Comparative Example 1A has an overall steam-to-ethylbenzene ratio is 1.00 kg/kg, and 62% of the total steam used in the reactors is generated in the process itself by a combination of azeotropic heat recovery and steam generation utilizing the heat of the reactor effluent. Thus, only 0.38 kg of heating steam per kg of ethylbenzene feed is available for interstage reheat and for heating the primary reactor feed. In Comparative Example 1A, the primary dehydrogenation reactor 1 inlet temperature necessary to convert 64% of ethylbenzene in the two reactor system is 650° C. In Comparative Example 1A, the mixture of ethylbenzene and feed steam leaves the feed/effluent exchanger 4 at 550° C. By heat balance, the heating steam has to be heated in the tertiary steam superheater 7 to a temperature of 1102° C. in order for the final primary reactor feed stream 34 mixture to reach the required 650° C. primary dehydrogenation reactor 1 inlet temperature. However, the 1102° C. temperature is well above the temperature limit of the Incoloy 800H/800 HT metallurgy (899° C.), used for the construction of the heating steam stream 29 transfer line and the primary reactor feed mixer 10.

In order to reduce the temperature of superheated heating steam stream 29 to 899° C., the amount of heating steam has to be increased from 0.38 kg to 0.63 kg per kg of ethylbenzene, which increases the operating cost, both due to the cost of the additional steam and the cost of additional fuel necessary to heat the steam. The data presented in Table 1 for the prior art process of Comparative Example 1B utilize the increased quantity of heating steam, i.e., 0.63 kg per kg of ethylbenzene, which is necessarily required to reduce the temperature of superheated heating steam stream 29 to 899° C.

TABLE 1

| | Example 1 | Comparative Example 1A | Comparative Example 1B |
|---|---|---|---|
| Overall Steam/Hydrocarbon Ratio (kg/kg) | 1.00 | 1.00 | 1.25 |
| Heating Steam/Hydrocarbon Ratio (kg/kg) | 0.38 | 0.38 | 0.63 |
| Hydrocarbon Flow (kg/hr) | 107345 | 107345 | 107345 |
| Stream 21 Temperature (° C.) | 155 | 155 | 155 |
| Stream 22 Temperature (° C.) | 448 | 550 | 441 |
| Stream 23 Temperature (° C.) | 850 | 850 | 810 |
| Stream 24 Temperature (° C.) | 596 | 596 | 619 |
| Stream 25 Temperature (° C.) | 789 | | |
| Stream 26 Temperature (° C.) | 565 | | |
| Stream 27 Temperature (° C.) | 899 | 899 | 772 |
| Stream 28 Temperature (° C.) | 643 | 643 | 648 |
| Stream 29 Temperature (° C.) | 899 | 1102 | 899 |
| Stream 32 Temperature (° C.) | 550 | 550 | 550 |
| Stream 33 Temperature (° C.) | 597 | | |
| Stream 34 Temperature (° C.) | 650 | 650 | 641 |
| Stream 35 Temperature (° C.) | 560 | 560 | 559 |
| Stream 36 Temperature (° C.) | 605 | 605 | 609 |
| Stream 37 Temperature (° C.) | 650 | 650 | 641 |
| Stream 38 Temperature (° C.) | 588 | 587 | 585 |
| Primary Radiant Coil (5) Duty ($10^6$ kcal/hr) | 8.78 | 6.65 | 13.16 |
| Secondary Radiant Coil (6) Duty ($10^6$ kcal/hr) | 6.83 | 6.83 | 5.60 |
| Tertiary Radiant Coil (7) Duty ($10^6$ kcal/hr) | 5.81 | 10.73 | 9.37 |
| Primary Convective Coil (8) Duty ($10^6$ kcal/hr) | 5.97 | 8.11 | 9.59 |
| Secondary Convective Coil (11) Duty ($10^6$ kcal/hr) | 4.28 | | |
| Economizing Coil (9) Duty ($10^6$ kcal/hr) | 4.52 | 12.59 | 7.19 |
| Superheater Fuel Consumption ($10^6$ kcal/hr) | 39.34 | 48.81 | 48.80 |
| External Steam Consumption ($10^6$ kcal/hr) | 22.53 | 22.53 | 37.03 |
| Total Energy Consumption ($10^6$ kcal/hr) | 61.87 | 71.33 | 85.83 |
| Net Energy Consumption (after Coil 11 credit) ($10^6$ | 57.35 | 58.74 | 78.65 |
| Annual Energy Cost at $5-15 per $10^6$ kcal (million USD) | 9.2-27.5 | 9.4-28.2 | 12.6-37.8 |
| Annual Savings (million USD) | 3.4-10.2 | N/A | Base |

As presented in Table 1, the process data of Comparative Example 1A, represent the schematic flow sheet of FIG. 1, On the other hand, the process data of Example 1 presented in Table 1 represent the inventive schematic flow sheet of FIG. 2. The process of FIG. 2 is different from prior art FIG. 1 in that the claimed flow process inventively utilizes a process feed preheater 12, and a secondary convection heating coil 11. The process feed preheater 12 preheats reactor feed stream 32 with preheating steam stream 25. Because the reactor feed stream 33 entering the feed mixer 10 is at a higher temperature than the rector feed steam 32 in the existing state of the art process, the heating temperature required to bring the first reactor feed to the desired temperature at the inlet to the first reactor is reduced in the methods and systems disclosed herein. Preheating steam stream 25 is ultimately provided by utilizing primary reheating steam stream 23 from primary steam superheater 5 in a heat transfer step to reheat the reactor effluent stream 35 (i.e., a high temperature chemical conversion apparatus effluent), in primary reheater 2A to provide cooled reheater steam stream 24, which is then forwarded to secondary convection heating coil 11. Secondary convection heating coil 11 advantageously utilizes the heat from combined flue gases 13 of primary, secondary, and tertiary steam superheaters 5, 6, and 7. Once preheating steam stream 25 exchanges heat with the reactor feed stream 32 in process feed preheater 12, it becomes cooled preheating steam stream 26, which is forwarded to secondary steam superheater 6 to provide secondary reheating steam stream 27.

In particular, the present inventive method and system, make it possible to keep the overall steam-to-ethylbenzene ratio at 1.00 kg/kg without violating the temperature limit of the Incoloy 80011/800 HT material because the temperature of the reactor feed entering the primary reactor feed mixer 10 is raised from 550° C. to 597° C. in the process feed preheater 12.

From the data presented in Table 1, in a facility producing 500 thousand metric tons of styrene annually, the net energy savings compared with the current state of the art process (after accounting for the energy recovered in the economizer coil 9) are $21.3 \cdot 10^6$ kcal/hour. This translates to annual savings of between 3.4 and 10.2 million USD (using a range of fuel prices between 20 and 60 USD per million kcal).

As mentioned earlier, the methods of this invention can also be applied to a system using direct heating for interstage reheat. In such a system, interstage reheating is accomplished by burning fuel in oxygen or air directly inside the reheater, as described in U.S. Pat. No. 8,084,660 to Welch et al., by selectively oxidizing hydrogen which comprises part of the primary reactor effluent, as practiced by the UOP-Lummus SMART process.

FIG. 3 depicts a flow scheme of the prior art in which direct heating is used, as described above. In FIG. 3 the low temperature steam stream 21 (which ultimately becomes heating steam) is first heated against the superheater flue gas stream 13 and is then heated to the final temperature in the radiant coil of the steam superheater 5, before being added as heating steam stream 29 to the reactor feed stream 32 in the primary reactor feed mixer 10.

Figure 4:
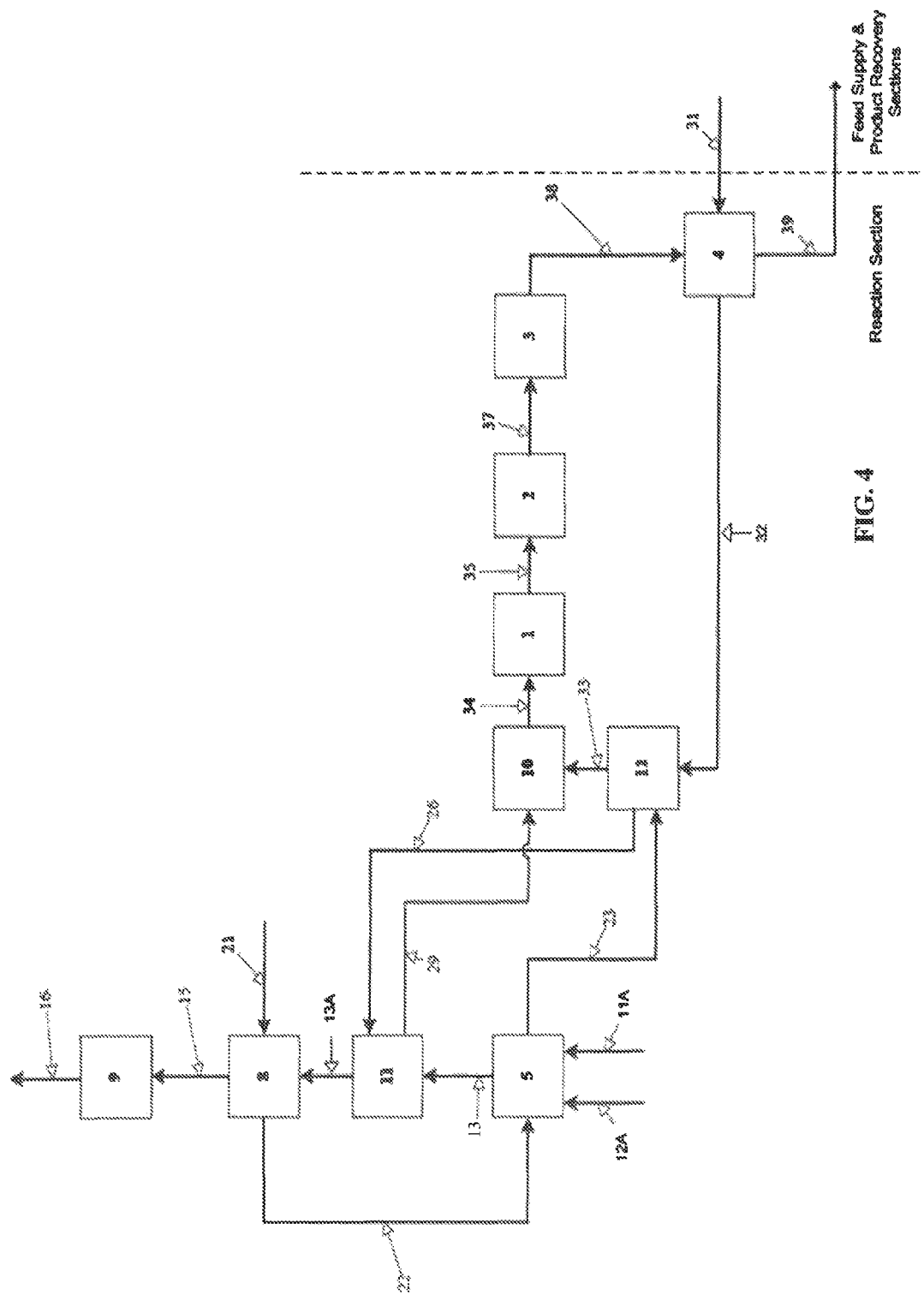
FIG. 4 is a schematic flowsheet illustrating an embodiment of the invention having a two-reactor system for producing styrene via dehydrogenation of ethylbenzene, with direct reheat.

FIG. 4 depicts a flow scheme embodiment of the invention as applied to a system using direct heating for interstage reheat. The key difference between the prior art process of FIG. 3, as described above, and the process of the various embodiments of the invention is the addition of a process feed preheater 12 and a secondary convection coil 11. The process feed preheater 12 takes the preheating steam stream 23 and uses it to preheat the reactor feed stream 32 to an intermediate temperature. The cooled preheating steam stream 26 from the process feed preheater 12 is directed to the secondary convection coil 11. The preheated feed stream 33 leaving the process feed preheater 12 is then brought to the primary reactor feed stream 34 mixture temperature by mixing it in the primary reactor feed mixer 10 with the heating steam stream 29 heated in the secondary convection coil 11. The feed stream is then reacted in primary reactor 1, before being passed as effluent stream 35 to reheater 2 and on to secondary dehydrogenation reactor 3 via effluent stream 37, to provide the final reactor product stream 38, which after exchanging heat with the reactor feed stream 31 becomes stream 39.

Figure 5:
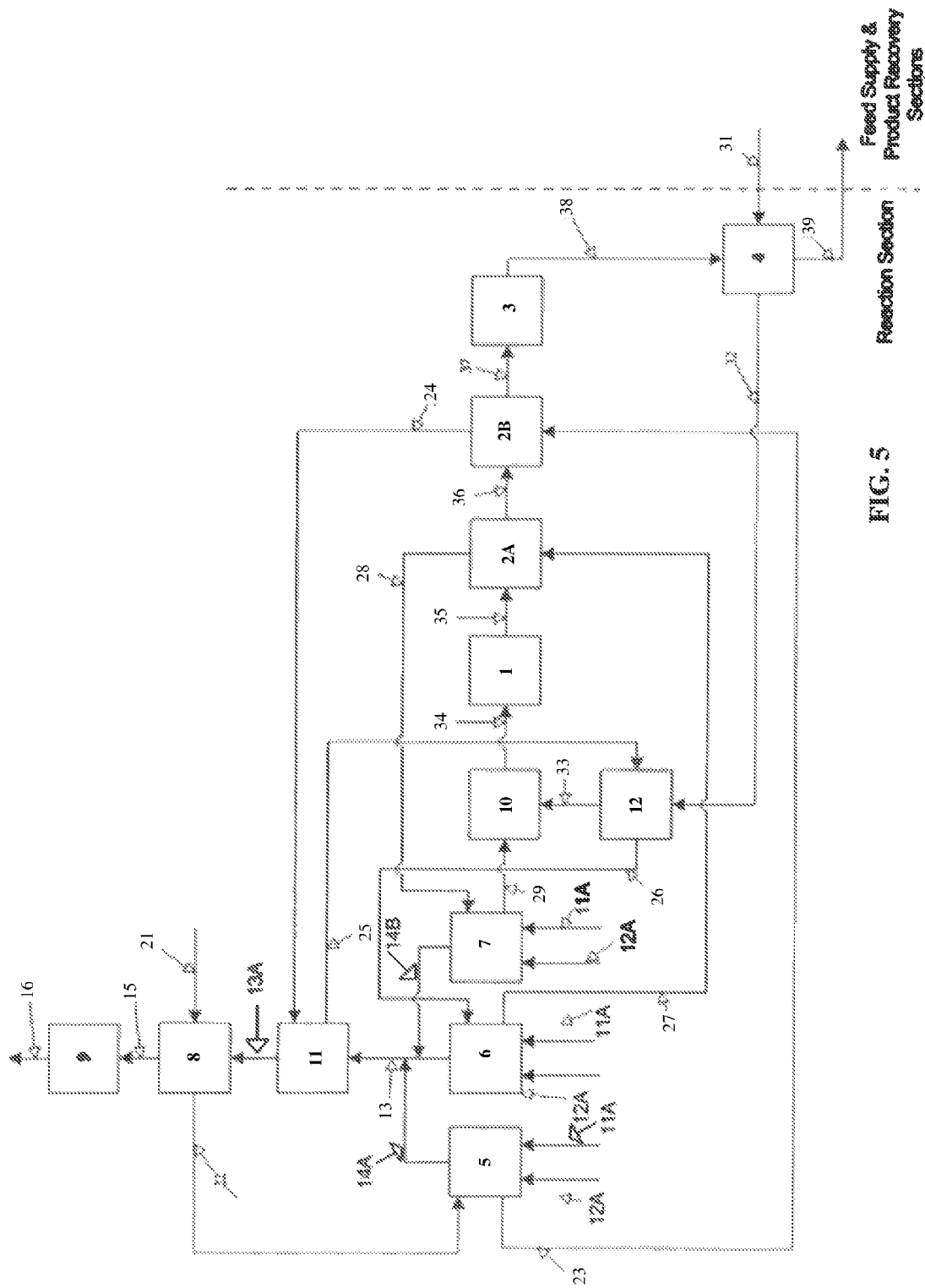
FIG. 5 is a schematic flowsheet illustrating an embodiment of the invention having a two-reactor system and a series of two reheaters for producing styrene via dehydrogenation of ethylbenzene, with steam reheat.

FIG. 5 presents an embodiment of the invention having a two-reactor system and a series of two reheaters for producing styrene via dehydrogenation of ethylbenzene. FIG. 5 presents the option of reheating steam stream 23 being directed to the series of two reheaters and specifically reheater 2B instead of reheater 2A. Reheating steam stream 27 coming from the fired heater 6 (i.e., secondary steam superheater) is directed to reheater 2A instead of reheater 2B.

Figure 6:
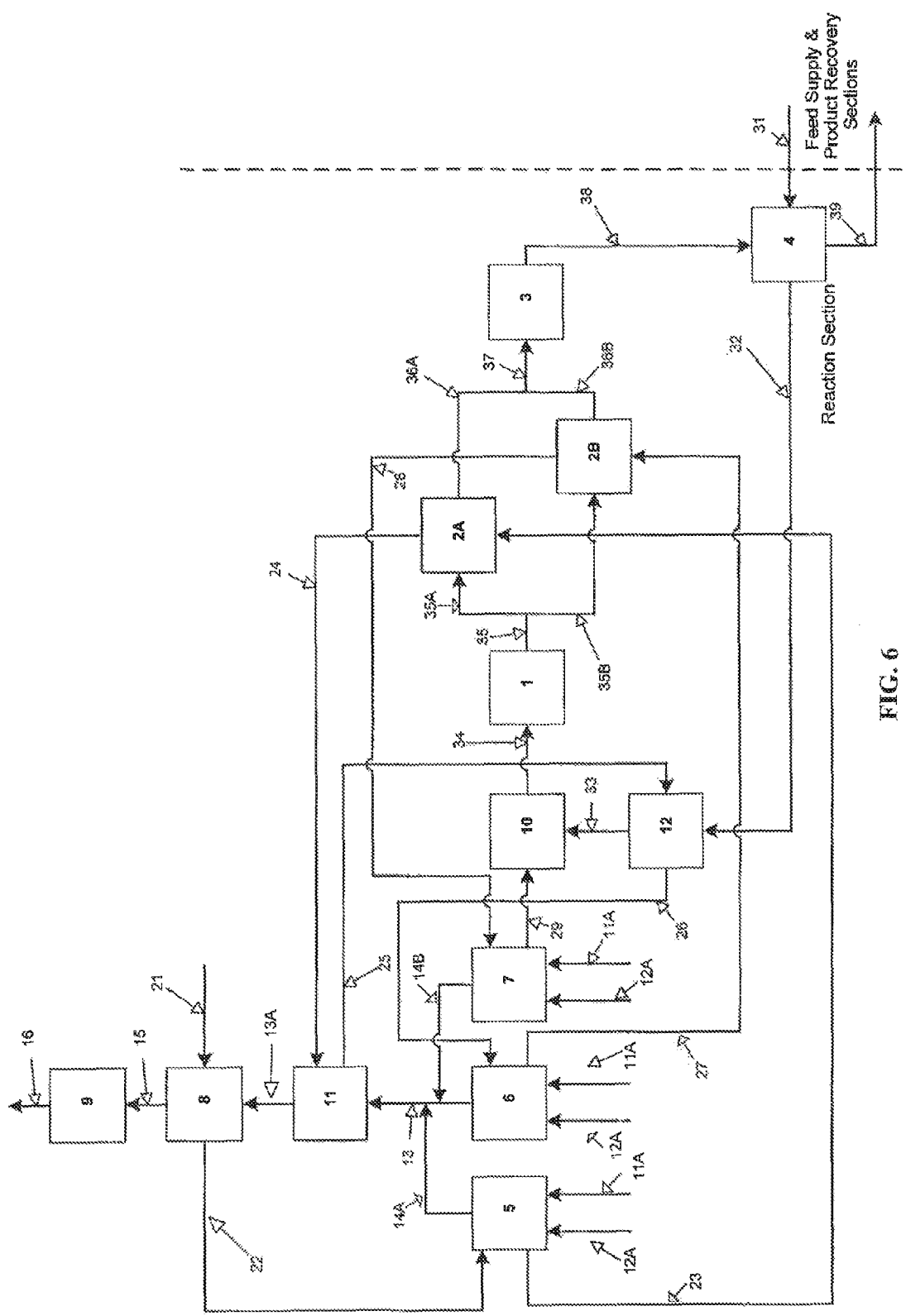
FIG. 6 is a schematic flowsheet illustrating an embodiment of the invention having a two-reactor system and two reheaters arranged in parallel for producing styrene via dehydrogenation of ethylbenzene, with steam reheat.
Figure 7:
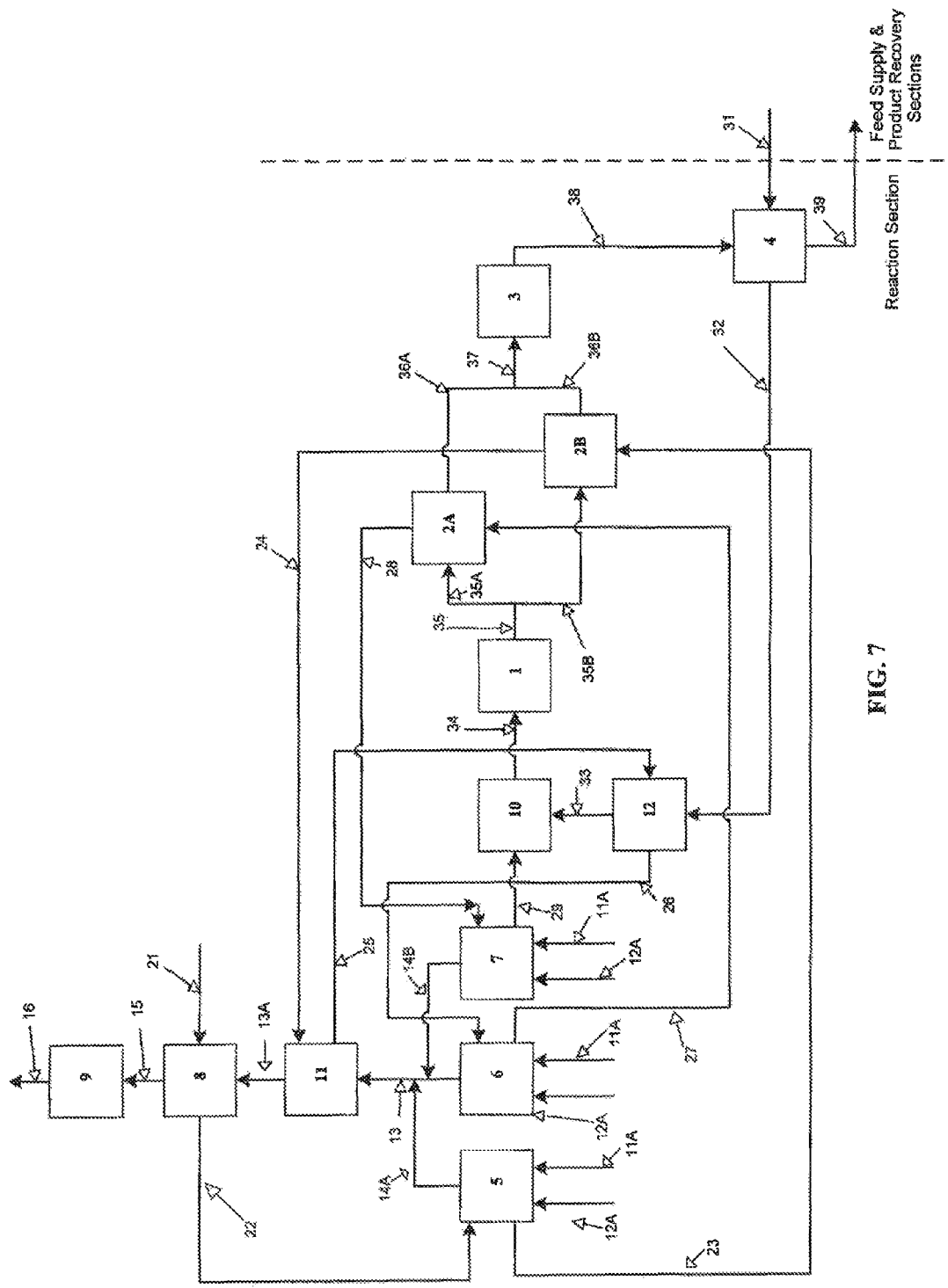
FIG. 7 is a schematic flowsheet illustrating an embodiment of the invention having a two-reactor system and two reheaters arranged in parallel for producing styrene via dehydrogenation of ethylbenzene, with steam reheat.

FIG. 6 presents an embodiment of the invention having a two-reactor system and two reheaters arranged in parallel. FIG. 6 presents the option of reheating steam stream 23 directed to reheater 2A and reheating steam stream 27 is directed to reheater 2B. FIG. 7 presents an embodiment of the invention having a two-reactor system and two reheaters arranged in parallel with the option of reheating steam stream 23 directed to reheater 2B and reheating steam stream 27 being directed to reheater 2A.

FIGS. 2 and 4 differ from one another as far as the source of steam used in the process feed preheater 12 and the destination of the steam leaving the secondary convection coil 11. In the case of a steam reheat based system of FIG. 2, the preheating steam used in the process feed preheater 12 comes from the secondary convection coil 11, while in the case of a direct heating based system of FIG. 4 the preheating steam comes from the primary steam superheater 5, and heating steam is heated in the secondary convection heating coil 11 before being directed to the primary reactor feed mixer 10.

The process data presented in Table 2 compare Comparative Examples 2A and 2B to an embodiment of the invention of Example 2. The Examples of Table 2 represent a system wherein a high amount of steam is generated in the process itself by a combination of azeotropic heat recovery and steam generation utilizing the heat of the reactor effluent. As such, the process parameters are identical to those in the Examples presented in Table 1, i.e., the overall steam-to-ethylbenzene ratio is 1.00 kg/kg, with 62% of the total steam used in the reactors being generated in the process itself by a combination of azeotropic heat recovery and steam generation using the heat of the reactor effluent, and the reactor feed being heated to 550° C. in the feed/effluent exchanger 4.

TABLE 2

|  | Example 2 | Comparative Example 2A | Comparative Example 2B |
|---|---|---|---|
| Overall Steam/Hydrocarbon Ratio (kg/kg) | 1.00 | 1.00 | 1.25 |
| Heating Steam/Hydrocarbon Ratio (kg/kg) | 0.38 | 0.38 | 0.63 |

TABLE 2-continued

| | Example 2 | Comparative Example 2A | Comparative Example 2B |
|---|---|---|---|
| Hydrocarbon Flow (kg/hr) | 107345 | 107345 | 107345 |
| Stream 21 Temperature (° C.) | 155 | 155 | 155 |
| Stream 22 Temperature (° C.) | 350 | 550 | 400 |
| Stream 23 Temperature (° C.) | 899 | | |
| Stream 24 Temperature (° C.) | | | |
| Stream 25 Temperature (° C.) | | | |
| Stream 26 Temperature (° C.) | 596 | | |
| Stream 27 Temperature (° C.) | | | |
| Stream 28 Temperature (° C.) | | | |
| Stream 29 Temperature (° C.) | 820 | 1104 | 899 |
| Stream 32 Temperature (° C.) | 550 | 550 | 551 |
| Stream 33 Temperature (° C.) | 615 | | |
| Stream 34 Temperature (° C.) | 650 | 650 | 641 |
| Stream 35 Temperature (° C.) | 561 | 561 | 560 |
| Stream 36 Temperature (° C.) | | | |
| Stream 37 Temperature (° C.) | 650 | 650 | 641 |
| Stream 38 Temperature (° C.) | 588 | 588 | 585 |
| Primary Radiant Coil (5) Duty ($10^6$ kcal/hr) | 10.08 | 12.78 | 17.94 |
| Secondary Radiant Coil (6) Duty ($10^6$ kcal/hr) | | | |
| Tertiary Radiant Coil (7) Duty ($10^6$ kcal/hr) | | | |
| Primary Convective Coil (8) Duty ($10^6$ kcal/hr) | 3.99 | 8.10 | 8.21 |
| Secondary Convective Coil (11) Duty ($10^6$ kcal/hr) | 4.97 | | |
| Economizing Coil (9) Duty ($10^6$ kcal/hr) | 1.54 | 5.22 | 4.47 |
| Superheater Fuel Consumption ($10^6$ kcal/hr) | 22.37 | 28.37 | 33.29 |
| External Steam Consumption ($10^6$ kcal/hr) | 22.53 | 22.53 | 37.03 |
| Total Energy Consumption ($10^6$ kcal/hr) | 44.90 | 50.89 | 70.32 |
| Net Energy Consumption (after Coil 11 credit) ($10^6$ | 43.35 | 45.67 | 65.84 |
| Annual Energy Cost at \$5-15 per $10^6$ kcal (million USD) | 6.9-20.8 | 7.3-21.9 | 10.5-31.6 |
| Annual Savings (million USD) | 3.6-10.8 | N/A | Base |

As expected, the Comparative Examples 2A and 2B, which represent the current state of the art methods, suffer from the same limitations as in Comparative Examples 1A and 1B, respectively. Specifically, the amount of heating steam available is insufficient to keep the temperature of the heating steam stream 29 at 899° C. or less. However, the improved method of Example 2 as exemplified in FIG. 4, preheats the reactor feed to 615° C. with 899° C. preheating steam originating in the primary steam superheater 5, and the former is then brought to the required 650° C. reactor inlet temperature by addition of heating steam heated in the secondary convection coil 11.

The methods of the claimed invention are equally well applicable to a system consisting of a single or multiple dehydrogenation reactors. The reactors can be adiabatic or isothermal, radial flow or axial flow type, or any combination of these characteristics. Furthermore, the methods of this invention are equally well applicable to styrene reaction systems featuring steam reheat and those featuring direct heating for interstage reheat, such as UOP-Lummus SMART process and the process disclosed in U.S. Pat. Nos. 8,193,404 and 8,084,660 to Welch et al. Also, the methods of this invention can be used with any catalyst suitable for dehydrogenation of ethylbenzene.

The terms "invention," "the invention," "this invention," and "the present invention" used in this patent are intended to refer broadly to all of the subject matter of this patent and the patent claims below. Statements containing these terms should not be understood to limit the subject matter described herein or to limit the meaning or scope of the patent claims below.

Although the embodiments of the present invention have been described in considerable detail with regard to certain versions thereof, other versions are possible, and alterations, permutations, and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. A method of heating a reactor feed in a multi reactor hydrocarbon dehydrogenation process comprising the steps of:
   (i) heating a first reheating steam stream against flue gas from one or more fired heaters, after the reheating steam stream heats a first reactor product stream in one or more first reactor product stream indirect heating apparatuses, to provide a preheating steam stream;
   (ii) heating a first reactor feed stream comprising a hydrocarbon and optionally feed steam, with the preheating steam stream in a first reactor feed stream indirect heating apparatus prior to entering a first reactor, to provide a preheated hydrocarbon stream and a cooled preheating steam stream;
   (iii) heating the cooled preheating steam stream in one of the one or more fired heaters to provide a second reheating steam stream;
   (iv) directing the second reheating steam stream to one of the one or more first reactor product stream indirect heating apparatuses to provide heat to the first reactor product stream and a cooled reheating steam stream;
   (v) heating the cooled reheating steam in one of the one or more fired heater to provide a heating steam stream; and (vi) mixing the heating steam stream with the preheated hydrocarbon stream prior to entering the first reactor.

2. The method of claim 1, wherein the first reactor product stream indirect heating apparatuses are arranged in series with respect to the first reactor product stream.

3. The method of claim 1, wherein the first reactor product stream indirect heating apparatuses are arranged in parallel with respect to the first reactor product stream.

4. The method of claim 1, wherein the cooled preheating steam stream of step (iii) is heated in a radiant section of one of the one or more fired heaters.

5. The method of claim 1, wherein the cooled reheating steam stream of step (v) is heated in a radiant section of one of the one or more fired heaters.

6. The method of claim 1, wherein the temperature of the heating steam stream is less than the limit set by the ASME Code for Alloy 800H/HT.

7. The method of claim 1, wherein the temperature of the heating steam stream is less than about 1700° F. (926.7° C.).

8. The method of claim 1, wherein the hydrocarbon is ethylbenzene.

9. The method of claim 1, wherein at least a portion of the first reactor feed steam is generated by azeotropic vaporization of a mixture of the hydrocarbon feed and water.

10. The method of claim 1, wherein the weight ratio of feed steam to hydrocarbon is at least 0.4.

11. The method of claim 1, wherein the weight ratio of total steam to hydrocarbon in the primary reactor feed stream is less than or equal to 1.25.

12. The method of claim 1, wherein the first reactor product stream indirect heating apparatuses and the first reactor feed stream indirect heating apparatus are shell and tube heat exchanger.

13. The method of claim 1, wherein said method is performed in a system, said system comprising: a means of heating a steam stream that has been used in a prior heat transfer step against flue gas from one or more fired heaters, and a means of indirectly transferring heat from said steam stream to a first reactor feed stream upstream of a first dehydrogenation reactor, wherein said steam stream, after transferring heat to the first reactor feed, is reheated to provide a subsequent heat transfer step.

14. The method of claim 13, wherein the prior heat transfer step is the heating of the first reactor product stream.

15. A method of heating a reactor feed in a multi reactor hydrocarbon dehydrogenation process, comprising the steps of:

i) heating a first reactor feed stream comprising a hydrocarbon, and optionally feed steam, in an indirect heating apparatus with a preheating steam stream from one of one or more fired heater, to provide a preheated hydrocarbon stream and a cooled preheating steam stream;

ii) heating the cooled preheating steam stream against flue gas from the one or more fired heaters to provide a heating steam stream; and iii) mixing the heating steam stream with the preheated hydrocarbon stream prior to entering a first reactor.

16. The method of claim 15, wherein the preheating steam stream of step (i) is heated in a radiant section of one of the one or more fired heaters.

17. The method of claim 15, wherein the indirect heating apparatus is a shell and tube heat exchanger.

18. The method of claim 15, wherein the temperature of the preheating steam stream is less than limit set by the ASME Code for Alloy 800H/HT.

19. The method of claim 15, wherein the temperature of the preheating steam stream comprising steam is less than about 1700° F. (927° C.).

20. The method of claim 15, wherein the hydrocarbon is ethylbenzene.

21. The method of claim 15, wherein at least a portion of the feed steam is generated by azeotropic vaporization of a mixture of the hydrocarbon feed and water.

22. The method of claim 15, wherein the weight ratio of feed steam to hydrocarbon is at least 0.4.

23. The method of claim 15, wherein the weight ratio of total steam to hydrocarbon in the first reactor feed stream is less than or equal to 1.25.

24. The method of claim 15, wherein said method is performed in a system, said system comprising: a means of indirectly transferring heat from a steam stream to a first reactor feed stream in a heat transfer step upstream of a first dehydrogenation reactor to provide a preheated feed stream; and a means of heating the steam stream after the heat transfer step against flue gas from one or more fired heaters; wherein said steam stream, after reheating is mixed with preheated feed stream prior to entering the first dehydrogenation reactor.

25. The method of claim 24, wherein the steam stream used in the heat transfer step is heated in a fired heater.

* * * * *